United States Patent [19]
Paulus et al.

[11] 4,075,245
[45] Feb. 21, 1978

[54] PROCESS FOR PREPARING SOLUTIONS OF N-METHYLOL-CHLOROACETAMIDE

[75] Inventors: Wilfried Paulus; Karl-Heinz Rullmann, both of Krefeld, Germany

[73] Assignee: Bayer Aktiengesellschaft, Leverkusen, Germany

[21] Appl. No.: 701,929

[22] Filed: July 1, 1976

[30] Foreign Application Priority Data

July 23, 1975 Germany .............................. 2532805

[51] Int. Cl.² ........................................... C07C 103/38
[52] U.S. Cl. .............................. 260/561 HL; 424/320
[58] Field of Search .................. 260/561 HL; 424/320

[56] References Cited

FOREIGN PATENT DOCUMENTS

2,351,821   4/1975   Germany.

OTHER PUBLICATIONS

Vail et al., J. Org. Chem. 27 (1962) p. 2067–2070.
Wagner et al., Synthetic Organic Chemistry, John Wiley & Sons, N.Y., 1955 pp. 568–569.

*Primary Examiner*—Arthur P. Demers
*Attorney, Agent, or Firm*—Burgess, Dinklage & Sprung

[57] ABSTRACT

Higly concentrated solutions of N-methylol-chloroacetamide are prepared by treating chloracetic acid methyl ester in solution in isopropanol with ammonia at temperatures of −20° to 10° C and then reacting with paraformaldehyde at temperatures of 60° to 120° C after the addition of water and a basic catalyst.

2 Claims, No Drawings

PROCESS FOR PREPARING SOLUTIONS OF N-METHYLOL-CHLOROACETAMIDE

BACKGROUND

This invention relates to a process for the preparation of highly concentrated solutions of N-methylol-chloroacetamide.

The preparation of N-methylol-chloroacetamide by reaction of chloroacetamide with formaldehyde in the presence of acids has been disclosed (Liebigs Ann. Chem. 343, 280 (1905)). However, this process suffers from a number of disadvantages, one being that N-methylol-chloroacetamide is obtained in low yields.

Furthermore it is known from German Published Specification No. 2,351,821 that the reaction products of chloroacetamide, alcohols and formaldehyde in the presence of potassium carbonate have a preservative and disinfectant action.

SUMMARY

A process for the manufacture of highly concentrated solutions of N-methylol-chloroacetamide has been found, in which chloroacetic acid methyl ester in solution in isopropanol is treated with ammonia at temperatures of −20° to 10° C and is then reacted with formaldehyde at temperatures of 60° to 120° C after addition of water and a basic catalyst.

DESCRIPTION

The process according to the invention can be explained by the following equation:

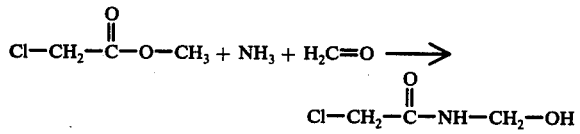

The chloroacetic acid methyl ester can be employed pure or in a commercially available quality. Slight impurities are of no significance as far as the process according to the invention is concerned.

The formaldehyde can of course also be employed in a polymeric form, for example as paraformaldehyde or meta formaldehyde, preferably as paraformaldehyde.

The concentration of the solution of chloroacetic acid methyl ester in isopropanol in the process according to the invention is preferably 20 to 85%, most preferably 50 to 60% by weight.

In the process according to the invention, generally 1 mol of chloroacetic acid methyl ester is reacted with an excess of ammonia, preferably 1 to 1.1 mols, and with an excess of formaldehyde, preferably 1 to 1.5 mols.

The amount of water employed is 40 to 50%, preferably 44 to 46% by weight, relative to the chloroacetic acid methyl ester.

Basic catalysts which may be mentioned are alkali metal carbonates and alkaline earth metal carbonates, such as potassium carbonate, sodium carbonate, sodium bicarbonate, calcium carbonate and barium carbonate, potassium carbonate being preferred. The amount of the catalyst employed is 2 to 5%, preferably 3 to 4% by weight, relative to the chloroacetic acid methyl ester.

The process according to the invention can be carried out as follows:

Gaseous ammonia is passed into the solution of chloroacetic acid methyl ester in isopropanol at −20° to 10° C, preferably at 0° to 5° C. After passing in the ammonia, water and a basic catalyst are added in the same reaction vessel, and the reaction mixture is reacted with formaldehyde at 60° to 120° C, preferably 80° to 90° C.

The reaction mixture is worked up by a method which is in itself known, by filtering off the catalyst and subsequently carrying out a fractional distillation. Preferably, however, the reaction mixture is not worked up further and instead is used directly as a microbicidal agent.

The process according to the invention provides an advantageous method of direct preparation of N-methylol-chloroacetamide solutions in concentrations of 35 to 45% by weight in a medium which is suitable for use as a microbicide. Since the solubility of N-methylol-chloroacetamide in the individual components is substantially lower (water 16.7% by weight, methanol 11.1% by weight, isopropanol 2.5% by weight), it is surprising that solutions containing 35 to 45% by weight of N-methylol-chloroacetamide can be prepared. The preparation of 35 to 45% strength by weight N-methylol-chloroacetamide solutions are advantageous from the point of view of the end use.

In addition to N-methylol-chloroacetamide, the solutions prepared by the process according to the invention contain formaldehyde, isopropanol, methanol and isopropylformal.

The process according to the invention provides an advantageous method of preparation of N-chloromethylol-acetamide solutions in a simple manner, with high yields and without intermediate isolation of the N-methylol-chloroacetamide.

The N-methylol-chloroacetamide solutions according to the invention are furthermore distinguished by the advantage of having a good odor. They are miscible with water in all proportions and can optionally be used in combination with other microbicidal agents.

The N-methylol-chloroacetamide solutions can be employed as microbicidal agents (German Published Specification No. 2,351,821).

EXAMPLE 4.42 kg of chloroacetic acid methyl ester (40.8 mols) and 3.5 kg of isopropanol are introduced into a 20 l flask, whilst stirring, and cooled to −20° C by external cooling. 0.74 kg of gaseous ammonia (43.5 mols) are passed into the mixture, whilst stirring, in such a way that the temperature of the mixture in the reaction vessel does not exceed +10° C. After the ammonia has been passed in, stirring is continued for about 10 hours in the temperature range of 10° to 20° C. 0.15 kg of potassium carbonate, dissolved in 2 l of water, is then added to the mixture. After stirring for 15 minutes, 1.6 kg of paraformaldehyde (53.4 mols) are added, again whilst stirring, and the mixture is warmed to 90° C by external heating. After 50 minutes at 90° C, the paraformaldehyde has depolymerised completely and the reaction has ended. A clear, colourless solution having a pH value of 4.0 is produced; it has the following composition: 40% by weight of N-methylol-chloroacetamide, 3% by weight of formaldehyde, 1% by weight of isopropylformal, the remainder consisting essentially of water, methyl alcohol and isopropanol.

What is claimed is:

1. Process for preparing a 35 to 45% strength by weight solution of N-methylol-chloroacetamide, which comprises treating chloroacetic acid methyl ester in solution in isopropanol with ammonia at temperatures of −20° to 10° C and then reacting with paraformaldehyde at temperatures of 60° to 120° C after the addition of water and a basic catalyst.

2. An aqueous solution of N-methylol-chloro-acetamide in a concentration of 35 to 45% by weight in a medium which contains formaldehyde, isopropanol, methanol and isopropylformal.

* * * * *